US010535244B2

(12) United States Patent
Treacy et al.

(10) Patent No.: US 10,535,244 B2
(45) Date of Patent: Jan. 14, 2020

(54) PATIENT MONITORING SYSTEM AND METHOD FOR ACTIVITY TRACKING

(71) Applicant: General Electric Company, Schenectady, NY (US)

(72) Inventors: Stephen Treacy, Milwaukee, WI (US); Matthew Grubis, New Berlin, WI (US); Scott Fuller, Greendale, WI (US); Eliana Stein, Madison, WI (US); Magnus Kall, Espoo (FI)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/456,929

(22) Filed: Mar. 13, 2017

(65) Prior Publication Data

US 2018/0261066 A1 Sep. 13, 2018

(51) Int. Cl.
*G08B 21/04* (2006.01)
*A61B 5/11* (2006.01)
(Continued)

(52) U.S. Cl.
CPC .......... *G08B 21/0453* (2013.01); *A61B 5/002* (2013.01); *A61B 5/1113* (2013.01);
(Continued)

(58) Field of Classification Search
CPC ..... A61B 5/0002; A61B 5/0022; A61B 5/021; A61B 5/0402; A61B 5/0472;
(Continued)

(56) References Cited

U.S. PATENT DOCUMENTS 6,434,258 B2   8/2002   Wiens
8,018,584 B1   9/2011   Amir
(Continued)

FOREIGN PATENT DOCUMENTS

KR    10-1587924 B1    1/2016
WO    2005/079122 A1   8/2005
WO    2014/209697 A1   12/2014

OTHER PUBLICATIONS

Gorges, Mattias et al., "Improving Alarm Performance in the Medical Intensive Care Unit Using Delays and Clinical Context", International Anesthesia Research Society, vol. 108, No. 5, May 2009.

(Continued)

*Primary Examiner* — Brian Wilson
(74) *Attorney, Agent, or Firm* — Andrus Intellectual Property Law, LLP (57) ABSTRACT

A patient monitoring system includes an identification transmitter that transmits an identification signal associated with a patient and a location tracking system having a plurality of identification receivers arranged in a care facility that receive the identification signal from the identification transmitter, wherein the location tracking system determines a patient location within a care facility based on a location of receipt of the identification signal. The patient monitoring system further includes an activity tracking module executable to receive at least one activity threshold for the patient and the patient location, and to determine a patient activity indicator based on the patient location. The activity tracking module is further executable to generate an activity alert based on a comparison between the patient activity indicator and the activity threshold.

14 Claims, 7 Drawing Sheets

(51) Int. Cl.
  *A61B 5/00* (2006.01)
  *G08B 25/01* (2006.01)
  *A61B 5/0402* (2006.01)
  *A61B 5/1455* (2006.01)
  *A61B 5/021* (2006.01)
  *A61B 5/0472* (2006.01)

(52) U.S. Cl.
  CPC ........ *A61B 5/1118* (2013.01); *G08B 21/0415* (2013.01); *G08B 21/0423* (2013.01); *G08B 21/0446* (2013.01); *G08B 25/016* (2013.01); *A61B 5/021* (2013.01); *A61B 5/0402* (2013.01); *A61B 5/0472* (2013.01); *A61B 5/1116* (2013.01); *A61B 5/14551* (2013.01); *A61B 5/6823* (2013.01); *A61B 5/6828* (2013.01); *A61B 2562/0219* (2013.01); *A61B 2562/08* (2013.01)

(58) Field of Classification Search
  CPC ... A61B 5/1113; A61B 5/1116; A61B 5/6802; A61B 5/6823; A61B 5/6828; A61B 5/7405; A61B 5/746; A61B 5/1118; A61B 5/002; A61B 2562/08; A61B 2562/0219; A61B 5/14551; G06F 19/3418; G08B 21/0415; G08B 21/0423; G08B 21/0446; G08B 21/0453; G08B 21/182; G08B 25/016
  See application file for complete search history.

(56) References Cited

U.S. PATENT DOCUMENTS

| | | | |
|---|---|---|---|
| 8,139,945 B1 | 3/2012 | Amir et al. | |
| 8,310,364 B2 | 11/2012 | Derks et al. | |
| 8,514,071 B2 | 8/2013 | Derks et al. | |
| 8,620,682 B2 | 12/2013 | Bechtel et al. | |
| 8,633,806 B2 | 1/2014 | Amir | |
| 8,708,903 B2 | 4/2014 | Tran | |
| 9,055,928 B2 | 6/2015 | McCombie et al. | |
| 9,219,984 B1 | 12/2015 | Amir | |
| 9,306,665 B1 | 4/2016 | Amir | |
| 9,341,700 B2 | 5/2016 | Amir et al. | |
| 2007/0136102 A1* | 6/2007 | Rodgers | A61B 5/1113 705/3 |
| 2007/0162304 A1* | 7/2007 | Rodgers | G06F 19/00 705/2 |
| 2011/0105854 A1* | 5/2011 | Kiani | G16H 40/63 600/300 |
| 2014/0077956 A1* | 3/2014 | Sampath | A61B 5/0022 340/573.1 |
| 2014/0145848 A1 | 5/2014 | Amir | |
| 2014/0247137 A1* | 9/2014 | Proud | G06F 19/3418 340/870.01 |
| 2014/0257047 A1 | 9/2014 | Sillay et al. | |
| 2015/0269824 A1* | 9/2015 | Zhang | G08B 21/0438 340/539.12 |
| 2016/0140827 A1* | 5/2016 | Derenne | G08B 21/043 340/573.7 |
| 2016/0157735 A1* | 6/2016 | Zhang | A61B 5/02055 600/301 |

OTHER PUBLICATIONS

International Search Report and Written Opinion issued in connection with corresponding PCT Application No. PCT/US2018/022113 dated Jul. 2, 2018.

* cited by examiner

PATIENT MONITORING SYSTEM AND METHOD FOR ACTIVITY TRACKING

BACKGROUND

The present disclosure relates generally to medical devices and, more specifically, to medical monitoring devices for monitoring a patient's physiology and health status, especially wireless monitoring devices and systems.

In the field of medicine physicians often desire to continuously monitor multiple physiological characteristics of their patients. Oftentimes, such monitoring of multiple physiological characteristics involves the use of several separate monitoring devices simultaneously, such as a pulse oximeter, a blood pressure monitor, a heart monitor, a temperature monitor, etc. Many standard patient monitoring devices are large and bulky, tethering the patient to bedside devices via physical wiring or cabling that inhibits patient movement and requires a patient to stay in one location or transport a large monitor with them when they move from one place to another, and this discourages, rather than encourages, patient movement. Thus, continuous monitoring has the potential to conflict with treatment and recovery goals involving patient mobility, where patient activity is encouraged and requiring a patient to be active is recommended for expediting patient recovery. However, wireless monitoring devices have been developed that are relatively small devices that can be fixed to the patient, such as wearable devices. Such wireless monitoring devices allow patients to move around more freely, thus enabling continuous monitoring of multiple physiological characteristics without inhibiting patient movement and discouraging speedy recovery.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

A patient monitoring system includes an identification transmitter that transmits an identification signal associated with a patient and a location tracking system having a plurality of identification receivers arranged in a care facility that receive the identification signal from the identification transmitter, wherein the location tracking system determines a patient location within a care facility based on a location of receipt of the identification signal. The patient monitoring system further includes an activity tracking module executable to receive at least one activity threshold for the patient and the patient location, and to determine a patient activity indicator based on the patient location. The activity tracking module is further executable to generate an activity alert based on a comparison between the patient activity indicator and the activity threshold.

In one embodiment, a method of monitoring a patient includes transmitting an identification signal associated with the patient from an identification transmitter and receiving the identification signal at an identification receiver, wherein one of the identification receiver or the identification transmitter is at a known location within a care facility. The method further includes determining a patient location within the care facility based on the known location of the identification receiver or the identification transmitter, determining a patient activity indicator based on the patient location, and generating an activity alert based on a comparison between the patient activity indicator and an activity threshold.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

The present inventors have recognized that a patient's activity level can have a significant impact on their health status and/or recovery while under medical care, such as recovery from a surgical procedure. Namely, encouraging a patient to engage in mental and physical activity can play an important role in providing recovery care and treatment to a patient. For example, encouraging a patient to stand, walk, or otherwise move can encourage recovery from a surgical procedure and expedite the path to normal bodily function and the patient's ability to go home sooner after a medical procedure. Additionally, studies have shown that lack of mental stimulation, due to patient isolation and lack of social interaction and/or visitation by family members or others can prolong a patient's recovery. While clinicians are aware of the importance of physical and mental activity for patients, tracking and assessing a patient's activity level can be difficult in busy care environments where clinicians have defined tasks and multiple clinicians each provide a limited aspect of the patient's care.

In view of the foregoing problems and challenges, the present inventors have recognized a need for an activity monitoring system and method that tracks a patient's activity level and automatically assesses whether the patient is sufficiently active to maximize the patient's medical treatment and encourage swift recovery. The disclosed patient monitoring system includes a location tracking system 40 that identifies a patient location 68 and an activity tracking module 24 that tracks the patient location 68 over time and determines a patient activity indicator over time, such as a value that represents or describes the patient's activity (e.g., laying, sitting, standing, walking) or activity level. The system then assesses the patient activity indicator against one or more activity thresholds set for the patient, such as based on their medical condition and/or care regimen. An activity alert can then be generated based on whether or not the patient's activity is meeting the prescribed minimum activity level. For example, the activity alert can be generated if the patient's activity level falls below the prescribed care regimen. In various embodiments, the activity alert may be presented to clinicians so that they can intervene, and assist and encourage the patient to engage in therapeutic activity. Alternatively or additionally, the activity alert may be presented to the patient and/or to the patient's family so that the patient and/or their family can proactively manage and maintain the patient's activity level.

The patient's activity level is determined based on the patient location identified by the location tracking system 40, and may also account for additional information measured from the patient. For example, the patient monitoring system may include an activity sensor, such as an accelerometer and/or a gyroscope, to provide information regarding the patient's position and motion at the measured location. Alternatively or additionally, the patient activity indicator determination may be further based on physiologic parameter data measured from the patient, such as heart rate and/or breath rate. Thereby, the patient activity indicator determination can be an accurate and precise measurement of the physical activity that the patient engaged in.

Alternatively or additionally, the patient activity indicator determination may also account for a patient's social interactions, such as visitations from friends and family, or even clinicians. Specifically, the location tracking system 40 may also be implemented to track the location of clinicians and visitors, such as providing a visitor notification when a visitor's location is tracked to the patient's location, especially to the patient's room or default location. Accordingly, such visitor interaction can be accounted for in tracking the patient's activity level, and the system can provide an alert if, for example, a patient has been alone for an extended period of time that exceeds a threshold.

Similarly, the system may make certain adjustments to operation of the sensing devices based on location, such as to prioritize recording and determining physiologic parameter data necessary to assess the patient's activity level when the patient is at certain locations where activity level information is especially important. Further, the system may be configured to avoid taking physiologic parameter measurements that interfere with or discourage a particular activity by the patient and/or do not assist in determining the patient's activity level. For example, the system may be configured to avoid taking a non-invasive blood pressure measurement while the patient is in a patient location associated with a physical therapy ward, since the non-invasive blood pressure measurements may interfere with the patient's activity and are unlikely to provide reliable blood pressure measurements while the patient is engaging in activity. As another example, the operation of the ECG sensing device may be adjusted to record a more limited set of cardiac information from the patient while the patient is in the physical therapy ward, focusing on robust measurements, such as heart rate, that can be more reliably measured while the patient is engaged in physical activity.

In various embodiments, a patient monitoring system 1 may include one or more wireless sensing devices (e.g. 3a-3c), each measuring different physiological parameter data from a patient. For example, the wireless sensing devices 3a-3c may be networked to a central hub or primary sensing device that determines a patient condition and regulates the various sensing devices in the network. In certain embodiments having a hub 15 (e.g. FIG. 1), the hub 15 may communicate with a central network for the medical care facility, e.g., host network 30. In another embodiment, the wireless sensing devices 3a-3c may communicate directly with the host network, which may coordinate and/or regulate the operation of the various sensing devices. Though the examples shown and described herein include a hub 15, it will be understood by a person having ordinary skill in the art that the monitoring and control methods discussed herein as being executed by the hub 15 may equally be executed by a host network 30. There, the wireless sensing devices may communicate with the host network directly, or indirectly, through the hub. For example, the hub may serve as an amplifier and/or router for communication between the wireless sensing devices and the host network. In such embodiments, each sensing device 3a-3c may process its own physiological parameter data and determine its own alarming conditions or such functions may be performed at the level of the host network.

Figure 1:
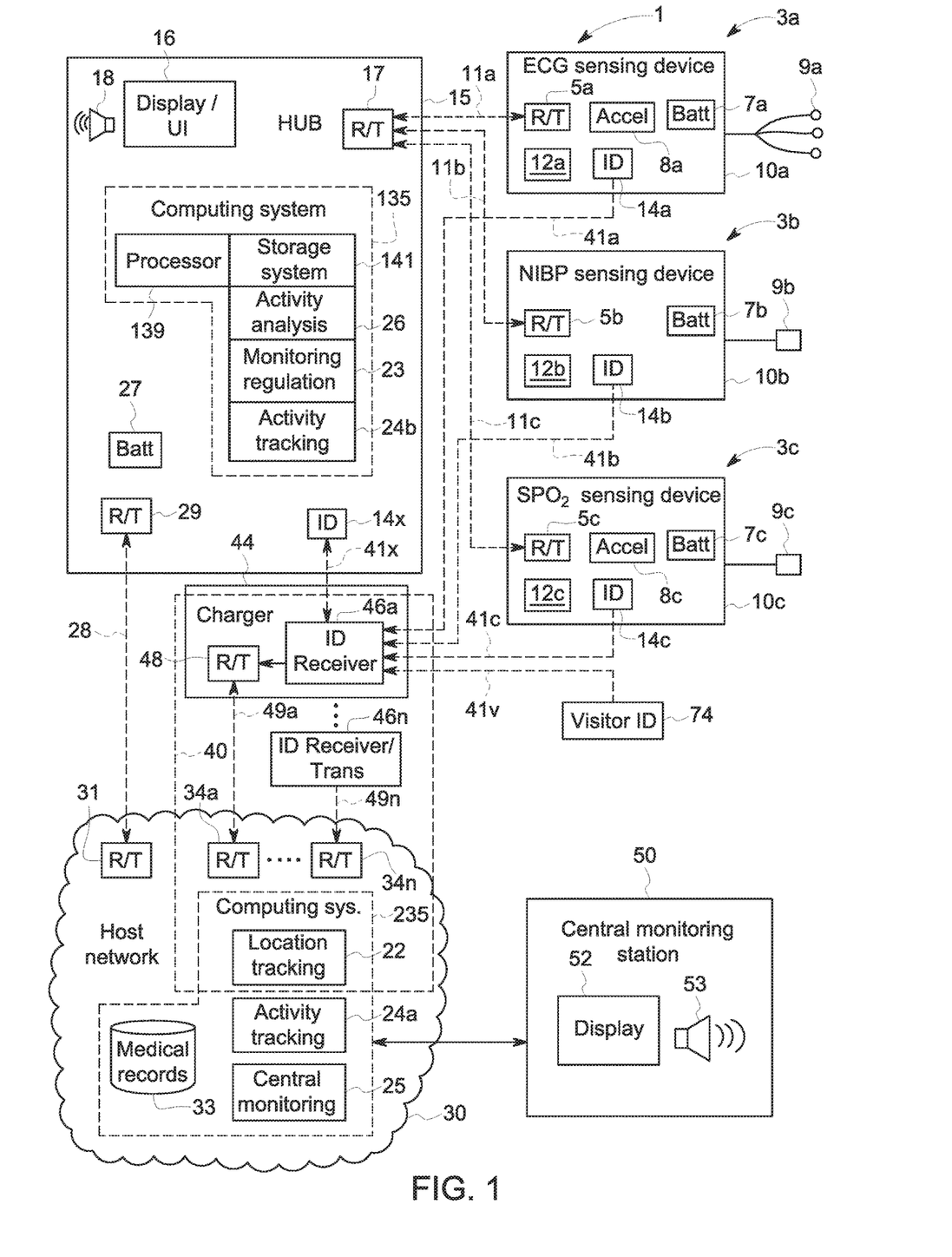
FIG. 1 is a schematic diagram of an exemplary patient monitoring system according to the present disclosure.

FIG. 1 depicts one embodiment of a patient monitoring system 1 containing three wireless sensing devices 3a-3c in wireless communication with a hub 15. The hub 15 is in wireless communication with a host network 30 that contains medical records database 33. For example, the hub device 15 may be attached to the patient's body, placed on or near the patient's bed, or positioned within range of the patient, such as in the same room as the patient. The hub device 15 may be a separate stand alone device, or it may be incorporated and/or housed with another device within the system 1, such as housed with one of the wireless sensing devices 3a-3c.

Each wireless sensing device 3a-3c contains one or more sensors 9a-9c for measuring physiological parameter data from a patient, and also includes a data acquisition device 10a-10c that receives the physiological parameter measurements from the sensors 9a-9c and transmits a parameter dataset based on those measurements to the hub device 15 via communication link 11a-11c. The sensors 9a-9c may be connected to the respective data acquisition device 10a-10c by wired or wireless means. The sensors 9a-9c may be any sensors, leads, or other devices available in the art for sensing or detecting physiological information from a patient, which may include but are not limited to electrodes, lead wires, or available physiological measurement devices such as pressure sensors, flow sensors, temperature sensors, blood pressure cuffs, pulse oximetry sensors, or the like. In the depicted embodiment, a first wireless sensing device 3a is an ECG sensing device having sensors 9a that are ECG electrodes. A second wireless sensing device 3b is a non-invasive blood pressure (NIBP) sensing device with a sensor 9b that is a blood pressure cuff including pressure sensors. A third wireless sensing device 3c is a peripheral oxygen saturation (SpO2) monitor having sensor 9c that is a pulse oximetry sensor, such as a standard pulse oximetry sensor configured for placement on a patient's fingertip. It should be understood that the patient monitoring system 1 of the present disclosure is not limited to the examples of sensing devices provided, but may be configured and employed to sense and monitor any physiological parameter of the patient. The examples provided herein are for the purposes of demonstrating the invention and should not be considered limiting.

The data acquisition device 10a-10c of each of the exemplary wireless sensing devices 3a-3c may include analog-to-digital (A/D) converters, which may be any devices or logic sets capable of digitizing analog physiological signals recorded by the associated sensors 9a-9c. For example, the A/D converters may be Analog Front End (AFE) devices. The data acquisition devices 10a-10c may further include processing units 12a-12c that receive the digital physiological data from the A/D converters and create physiological parameter data for transmission to the hub device 15 and/or to the host network 30. Each data acquisition device 10a-10c may be configured differently depending on the type of wireless sensing device, and may be configured to perform various signal processing functions and/or sensor control functions. To provide just a few examples, the processing unit 12a in the ECG sensing device 3a may be configured to filter the digital signal from the ECG sensors 9a to remove artifact and/or to perform various calculations and determinations based on the recorded cardiac data, such as heart rate, QRS interval, ST-T interval, or the like. The processing unit 12b in the NIBP monitor 3b may be configured, for example, to process the physiological data recorded by the sensors 9b in a blood pressure cuff to calculate systolic, diastolic, and mean blood pressure values for the patient. The processing unit 12c of the SpO2 sensing device 3c may be configured to determine a blood oxygenation value for the patient based on the digitized signal received from the pulse oximetry sensor 9c.

Accordingly, the processing unit 12a-12c may develop physiologic parameter data that, in addition to the recorded physiological data, also includes values measured and/or calculated from the recorded physiological data. The respective processing units 12a-12c may then control a receiver/transmitter 5a-5c in the relevant wireless sensing device 3a-3c to transmit the physiologic parameter data to the hub device 15 via communication link 11a-11c. The physiologic parameter data transmitted from the respective wireless sensing devices 3a-3c may include the raw digitized physiological data, filtered digitized physiological data, and/or processed data indicating information about the respective physiological parameter measured from the patient. Additionally, one or more of the data acquisition devices 10a-10c may be configured to compare the physiologic parameter data to one or more alarm thresholds to determine the presence of an alarm condition.

In other embodiments, the processing units 12a-12c may not perform any signal processing tasks and may simply be configured to perform necessary control functions for the respective wireless sensing device 3a-3c. In such an embodiment, the parameter data set transmitted by the respective processing unit 12a-12c may simply be the digitized raw data or digitized filter data from the various sensor devices 9a-9c.

The receiver/transmitter 5a-5c of each wireless sensing device 3a-3c communicates via the respective communication link 11a-11c with the receiver/transmitter 17 of the hub device 15, which may include separate receiving and transmitting devices or may include an integrated device providing both functions, such as a transceiver. The receiver/transmitters 5a-5c of the wireless sensing devices 3a-3c and the receiver/transmitter 17 of the hub device 15 may be any radio frequency devices known in the art for wirelessly transmitting data between two points. In one embodiment, the receiver/transmitters 5a-5c and 17 may be body area network (BAN) devices, such as medical body area network (MBAN) devices, that operate as a wireless network. For example, the wireless sensing devices 3a-3c may be wearable or portable computing devices in communication with a hub device 15 positioned in proximity of the patient. Other examples of radio protocols that could be used for this purpose include, but are not limited to, Bluetooth, Bluetooth Low Energy (BLE), ANT, and ZigBee.

In various embodiments, one or all of the sensing devices 3a-3c may be equipped with an identification transmitter 14a-14c that emits an identification signal that is detected by a location tracking system 40. The location tracking system 40 receives the identification signal in order to determine the patient's location. The tracking system 40 may be, for example, a real-time location system (RTLS) that provides immediate or real time tracking of the patient's location. In the embodiment of FIG. 1, each sensing device 3a-3c includes an identification transmitter 14a-14c that transmits an identification signal associated with the patient. Since the sensing devices 3a-3c are body-worn devices, the identification signal can be used to determine a patient location within the care facility. A plurality of identification receivers 46a-46n are placed at known locations throughout a care facility. The identification signal transmitted by the identification transmitter 14a-14c is thus received by one of the identification receivers 46a-46n closest to, or otherwise arranged to receive transmissions from, identification transmitters at that particular location of the patient. Each identification receiver 46a-46n then communicates the identification signal, along with its own receiver identification, to a location tracking module 22 that monitors and determines the patient location for the location tracking system 40 within the care facility. For example, the identification receiver 46a, 46n may communicate the identification signal and its own identification with a host network 30 for the care facility.

The location tracking module 22 then determines a patient location based on which identification receiver 46a-46n receives the identification signal for that patient from one or more of the identification transmitters 14a-14c. Specifically, the location tracking module 22 accesses a map or database of the care facility where each identification receiver 46a-46n is associated with a particular location in the care facility. The database associating each identification receiver 46a-46n with a location in the care facility may be, for example, uploaded and stored in the computing system 235 of the host network 30 as part of the system configuration.

Figure 4:
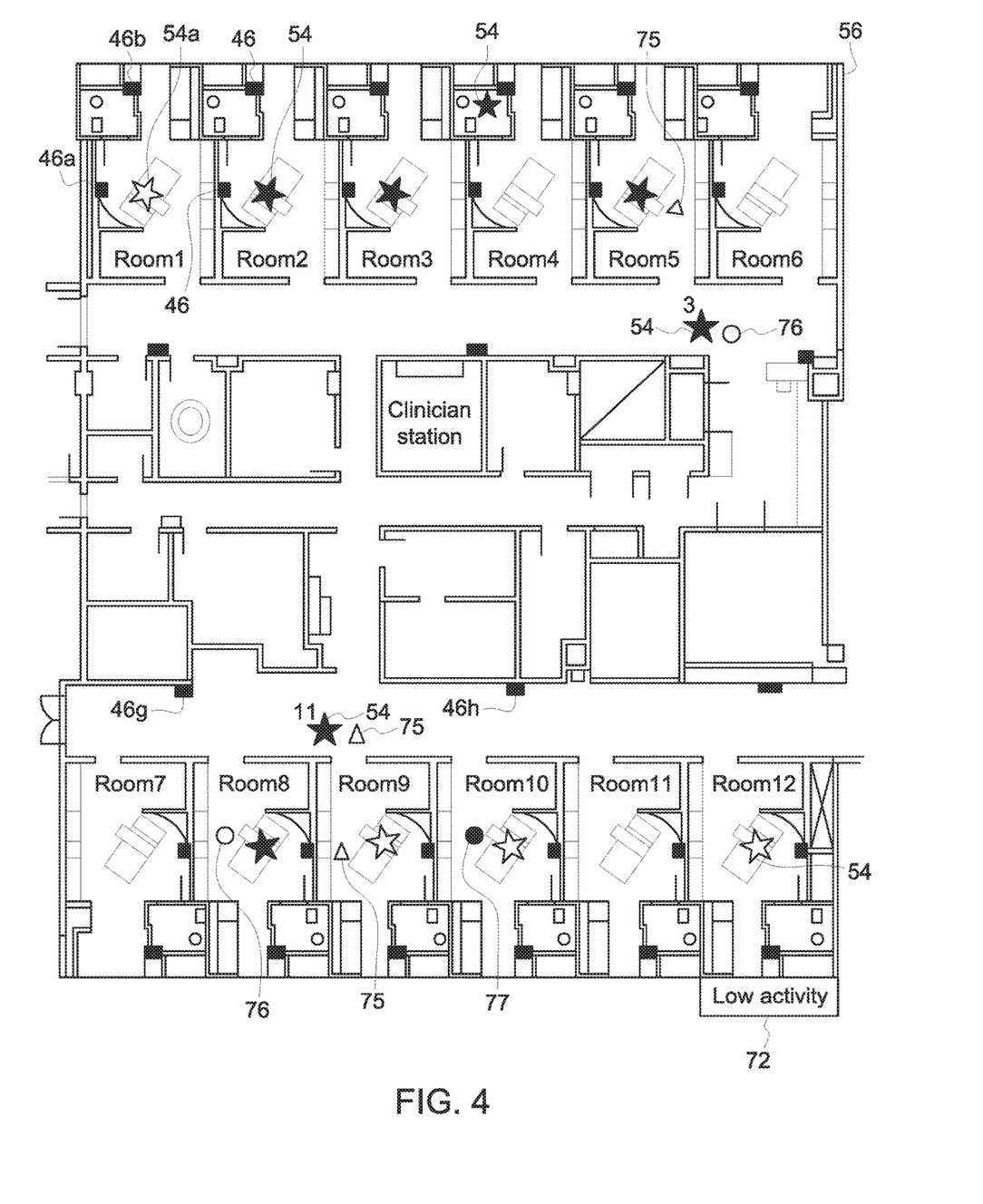
FIG. 4 is an exemplary embodiment of a display providing an activity alert.

FIG. 4 exemplifies a user interface display 56 (such as one that might be shown on a display 52 of a central monitoring station 50). A map, or layout, of a care facility is overlaid with multiple indicators showing the locations of various individuals and devices within the depicted care facility. For example, the display 56 shows the assigned locations of multiple identification receivers 46a-46n within a particular area of a care facility. For example, one or more identification receivers 46 are provided in each patient room and multiple identification receivers 46 are located in the hallways. The system is configured such that the identification signal emitted by the one or more identification transmitters 14 on the patient is picked up by one of the identification receivers 46, thereby establishing the current patient location.

In the exemplary user interface display 56 shown in FIG. 4, patient location indicators 54a-54n illustrate the current, or last measured, patient location determined by the location tracking system 40. Accordingly, the user interface display 56 illustrates the patient locations of multiple patients in a particular care facility, or section thereof. In certain embodiments, the patient location indicators 54a-54n may also convey information about a patient's activity, such as a patient's position and/or motion. Additionally, the user interface display 56 may display one or more location indicators of other individuals, such as a visitor location indicator 75, nurse location indicator 76, and a physician location indicator 77.

Accordingly, various individuals occupying a care facility may have identification transmitters transmitting an identification signal that is associated to them, or at least to their role in the care facility. Referring to FIG. 1, a visitor in a care facility may have a visitor identification transmitter 74 that transmits a visitor identification signal identifying them as a visitor to the location tracking system 40. The visitor identification transmitter 74 transmits the visitor identification signal via communication link 41v to a respective identification receiver 46a, 46n of the location tracking system 40. As described above, such communication may be by any of various wireless means depending on the configuration of the location tracking system 40. Similarly, clinicians may also carry identification transmitters on their person. For example, each clinician may carry an identification transmitter corresponding to their role in patient care, such as nurses carrying nurse location transmitters, physicians carrying physician location transmitters, etc. Alternatively, each clinician may carry a location transmitter that transmits an identification signal associated with that individual clinician within the location tracking system 40. The locations of the various clinicians can then be displayed, such as on the exemplary user interface display 56 of FIG. 4. Thereby, a single graphical depiction presents the locations of all individuals within a care facility, or within an area of a care facility.

In certain embodiments, the sensing devices 3a-3c my coordinate their transmission of the identification signal by the identification transmitters 14a-14c so that the transmissions are spaced out in time. Thereby, the identification signal can be transmitted more frequently and redundancy between the sensing devices 3a-3c can be reduced. Such coordination provides an efficient use of resources, including battery power, because it limits the frequency at which each sensing device transmits the identification signal. In other embodiments, the identification transmitters 14a-14c may independently and/or simultaneously transmit the identification signal, which may be used to provide redundancy and certainty to the patient location determination. In certain embodiments, the identification signal transmitted by the identification transmitters 14a-14c may be identical to one another, or may be different identification signals that are each associated with the patient.

The hub 15 may also include an identification transmitter 14x that transmits a location of the hub 15. Such identification transmitter 14x in the hub 15 may be in lieu of or in addition to the identification transmitters 14a-14c in the sensing devices. In embodiments where the hub 15 is a small, body-worn device that is attached to the patient, the identification transmitter 14x in the hub 15 may be sufficient for patient location tracking purposes. In embodiments where the hub 15 is not a body-worn device, the identification transmitter 14x may be unreliable, by itself, for patient location tracking. In such embodiments, the identification transmitter 14x may be used for tracking the location of the hub 15 separately from the patient.

Identification receivers 46 may be provided at fixed locations throughout the care facility, such as at each room, bed, bay, hallway, etc. to enable tracking the patient's location throughout the care facility. Each patient 4 and their associated wireless monitoring system may be assigned a primary identification receiver 46. For example, the primary identification receiver (e.g., 46a) may be located at the location where the patient is likely to spend the most time, such as the patient's assigned room, bed, bay, etc. For example, each patient room may be equipped with an identification receiver 46 dedicated to that room, which may then be associated to the patient when the patient 4 is assigned to that room. Any identification signal received by the primary identification receiver 46a is assumed to indicate that the patient is located in their assigned room.

In certain embodiments, each patient room may be equipped with multiple identification receivers 46 which may provide detailed information about the patient's location within their room. In such an embodiment, one of the identification receivers 46 may be identified as the primary identification receiver (e.g. 46a) which, for example, may be associated with the patient's bed. In the exemplary scenario shown in FIG. 4, each patient room has two identification receivers 46. The primary identification receiver (e.g. 46a for the patient 54a assigned to room one) receives the identification signal when the patient is in their bed or in the main part of their room. A second identification receiver (e.g. 46b) is located in the bathroom of the patient's room. Thus, the location tracking system 40 can identify when the patient 54a goes into the bathroom of their assigned room, namely when the identification signal is received by the identification receiver 46b in the patient's bathroom. Such information may be important for tracking the patient's bathroom activity, and/or for finding the patient quickly should an alarm condition occur.

In certain embodiments, the primary identification receiver (e.g., 46a for patient 54a) may be provided in a charger 44 associated with the monitoring system, such as associated with one or more of the sensing devices 3a-3c. As the charger 44 is a device that must remained plugged in to a power source, such as a wall outlet, the charger 44 is not a portable device and thus remains at a relative fixed location during a monitoring period. For example, the charger 44 may remain plugged in to a wall outlet in a patient's room, or otherwise remain plugged into a particular power source. Thus the charger 44 remains at a relative fixed and known location—e.g., movement of the charger 44 is restricted by the length of the power cord connecting it to the power source. Accordingly, the charger 44 provides a reliable fixed and known location for placement of the identification receiver in a patient's room.

For example, each sensing device 3a-3c may have a battery 7a-7c that is charged by the respective charger 44. The battery 7a-7c may be a removable battery that can be removed from the respective sensing device 3a-3c and placed on the charger 44 for charging, and a replacement battery may be inserted into the respective sensing device 3a-3c. For example, all of the sensing devices 3a-3c may utilize identical batteries 7a-7c, and thus the charger 44 may provide a bank of charging slots where batteries can be swapped and charged as each sensing device requires. Alternatively, the charger 44 may be configured to connect to each respective sensing device 3a-3c in order to charge the respective batteries 7a-7c. Likewise, the charger 44 may be configured to charge a battery 27 of the hub 15.

The identification transmitters 14a-14c, 14x communicate with one of a plurality of identification receivers 46a, 46n via a respective communication link 41a-41c, 41x. The communication link 41a-41c, 41x may be by any of various wireless communication protocols and/or platforms, such as Bluetooth, Bluetooth Low Energy (BLE), ZigBee, Wi-Fi, infrared, ultrasound, or by other wireless communication means. In certain embodiments, it is preferable that the transmission range of the identification signal be limited so that the identification transmitters 14a-14c, 14x are only within communication range of one identification receiver 46a-46n at a time. Thus, it may also be beneficial if the system is configured such that the communication signals and protocols do not pass through walls or other structural barriers so that identification receivers 46a, 46n can be placed in adjacent rooms, such as adjacent hospital rooms, without concern of cross-receiving. Accordingly, infrared may provide a good means for the communication links 41a-41c, 41x in other embodiments where line-of-sight limitations are prohibitive, other relatively short-range protocols may be desirable, such as Bluetooth, Bluetooth Low Energy (BLE), or ZigBee, or the like.

The identification receiver 46a, 46n may communicate with the host network via a separate receiver/transmitter that communicates with a respective receiver/transmitter 34 associated with the host network 30. Alternatively, one or more of the identification receivers 46a-46n may have a transmitter incorporated therein capable of transmitting the identification signal and its own receiver identifier to a respective receiver/transmitter 34n associated with the host network 30. The identification signal is communicated to the host network 30 via a respective communication link 49a-49n, which may be by any wireless or wired means and according to any communication protocol. For example, communication may be via a Wi-Fi network for the care facility, or by a dedicated wireless network for the location tracking system 40. For example, in certain embodiments the location tracking system 40 may employ one or more wireless local area networks (WLANs) situated throughout a care facility. In other embodiments, the devices on the location tracking system 40 may utilize the (WMTS) spectrum.

In certain embodiments, the identification transmitter 14a-14c, 14x may be incorporated into the receiver/transmitter 5a-5c, 17 associated with the respective sensing device 3a-3c and/or hub 15. In such an embodiment, the identification signal may be transmitted by the respective receiver/transmitter 5a-5c, 17, such as on the same network as the physiologic parameter data. For example, in an embodiment where the sensing devices 3a-3c communicate directly to a host network 30, the identification signal may be transmitted in conjunction with the physiological parameter data, which are received at a receiver associated with the host network 30, wherein the receiver is at a known location in the care facility.

In the embodiment depicted in FIG. 1, the identification transmitters are provided in the sensing devices 3a-3c and/or the hub 15 with the identification receivers 46a-46n provided at fixed and known locations throughout the care facility. In other embodiments, the identification receivers 46a-46n may travel with the patient, such as provided in the sensing devices 3a-3c and/or the hub 15 (and the identification transmitters 14 may be provided at fixed locations throughout the care facility). In such an embodiment, the respective sensing devices 3a-3c or hub 15 would receive the identification signal from a nearby identification transmitter 14 and may be equipped to determine its own location based on the identification signal received.

The location tracking module 22 is configured to receive the identification signal associated with the patient as well as the identification of the receiver 46a, 46n that received that identification signal for the patient. Based thereon, the location tracking module 22 determines a patient location within a care facility. For example, the location tracking module 22 may be configured with a map of a care facility, where a location of each identification receiver 46a-46n is associated to a location on the map. Thus, when an identification signal is received at a particular identification receiver 46a, 46n, the location tracking module 22 determines the patient location for the patient associated with the identification signal to be a given location range on the map of the care facility associated with the identification receiver 46a, 46n that received the identification signal. For example, the patient location may be determined to be the patient room associated with the identification receiver 46a assigned to or associated with that room.

As a patient moves throughout a care facility, the identification signal transmitted by the identification transmitters 14a-14c, 14x associated with the patient are received by different identification receivers 46a, 46n, and the location tracking module 22 may update the patient's location as a new identification receiver 46a, 46n reports receiving the identification signal. Additionally, the location tracking module 22 may store the patient location in order to track and store the patient's location over time. For example, a location pattern may be stored and generated for a patient's stay at a particular care facility.

The hub device may further include computing system 135 having processor 139 and storage system 141. The hub device 15 may serve to control the wireless sensing devices 3a-3c, and thus may transmit operation commands to the respective wireless sensing devices 3a-3c via the communication link 11a-11c to control their monitoring operations. The hub 15 may contain a monitoring regulation module 23 that is a set of software instructions stored in memory and executable on the processor to assess the physiologic parameter data collected by the wireless sensing devices 3a-3c and determine a patient condition therefrom, and to control the respective wireless sensing devices 3a-3c according to the patient condition. For example, the patient condition may be determined by comparing the physiologic parameter data collected by one or more of the sensing devices 3a-3c with alarm limits to determine whether the patient condition requires generating an alarm to alert the clinician to the patient's condition.

An activity tracking module 24 receives the patient location 68 (FIG. 3), such as from the location tracking module 22, and determines a patient activity indicator 70. For example, the activity tracking module 24 may include logic executable to associate an activity indicator with a particular patient location 68, or pattern of patient locations 68. For instance, if the patient location 68 is determined to be the bathroom, then the activity indicator may indicate the patient's use of the bathroom, thereby making a record of the patient's occupancy of the bathroom which may be helpful to a clinician assessing the patient's progression towards recovery. As another example, the patient location 68 may indicate a pattern associated with the patient going on a walk, such as the patient location 68 being detected at a pattern of identification receivers 46 starting in the patient's room and extending down a hallway and back to the patient's room at a pace associated with the patient walking. There, the patient activity indicator 70 may indicate that the patient went on a walk, and may also include indication of the length of time, distance, and/or rate of the patient's walk. As another explanatory example, if the patient location 68 is one associated with a physical therapy ward of a care facility, the patient activity indicator 70 may indicate that the patient engaged in physical therapy. Such information may then be recorded, such as in the patient's medical record 33 and may be provided to a clinician assessing the patient.

The patient activity indicator 70 may describe an activity or an activity class based on the patient location and/or information from the activity analysis module 26 (e.g. using bathroom, sleeping, laying, reclining, sitting upright, standing, walking, physical therapy). Alternatively or additionally, the patient activity indicator 70 may assign an activity level based on the patient location and/or information from the activity analysis module 26, where each location or a pattern of locations is assigned to an activity level. For example, level zero may indicate that the patient is at their default location (e.g. in their bed) and level five may indicate high activity for that patient (e.g. physical therapy, a relatively brisk walk of significant distance or time relative to the patient's condition, etc.).

The activity tracking module 24 may automatically track the patient's activity by comparing the patient's patient activity indicator 70 to one or more activity threshold(s) 67 set for the patient. For example, prescribed activity requirements may be set for a patient, such as activity that must be performed by the patient independently prior to releasing the patient from the care facility or moving the patient to a lower-acuity care unit. The prescribed activity requirements may be translated to or represented by activity thresholds 67, so that the system 1 can automatically assess whether the prescribed activity requirements have been met or whether the patient is progressing toward such requirements. To provide just one example, prescribed activity requirements may be set regarding the patient's ability to walk a threshold distance. There, activity thresholds 67 may represent the patient walking that distance, or may be a progressive increasing activity minimums per unit time that represent progress toward that goal of walking that distance—e.g., standing a predetermined amount, taking a few steps, longer walks, etc.

The activity tracking module 24 is configured to determine the patient activity indicator 71 accordingly so that the activity indicator 70 can be compared to the activity threshold 67. The activity tracking module 24 may then generate an activity alert 72, e.g., to alert clinicians and/or the patient to a deficiency in the patient's activity or to the patient's achievement of one or more activity thresholds. For example, the activity alert 72 may be an activity deficiency alert intended to bring attention to the patient's inactivity so that clinicians or the patient can intervene in order to increase the patient's activity level. Alternatively or additionally, the activity alert 72 may be intended to alert the clinician of the patient's achievement of the activity threshold 67, such as to alert a clinician when a patient has met requirements to be sent to a lower-acuity care facility.

In certain embodiments, the patient activity indicator 70 may further be based on one or more activity sensors 8 attached to the patient and measuring the patient's position and/or motion. In the depicted embodiment, the hub 15 contains an activity analysis module 26 that receives information from one or more activity sensors 8 attached to the patient. With reference to the exemplary embodiment of FIG. 1, the ECG sensing device 3a and the SPO2 sensing device 3c each contain an activity sensor 8a, 8c that monitors a position and/or motion of the respective data acquisition unit 10a, 10c, which is attached at a location on the patient's body. In one exemplary embodiment, the activity sensor 8a-8c may include an accelerometer, such as a three-axis accelerometer, a gyroscope, such as a three-axis gyroscope, or a combination accelerometer/gyroscope sensor. In still other embodiments, the activity sensor(s) 8a-8c may be another type of inertial sensor, such as including a magnetometer and/or any other type of sensor capable of acting as an accelerometer and/or a gyroscope.

Figure 2A:
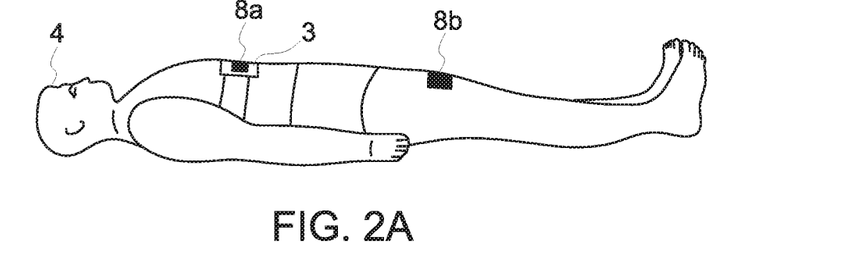
FIGS. 2A-2B depict embodiments of activity sensors connected to a patient as part of a patient monitoring system.
Figure 2B:
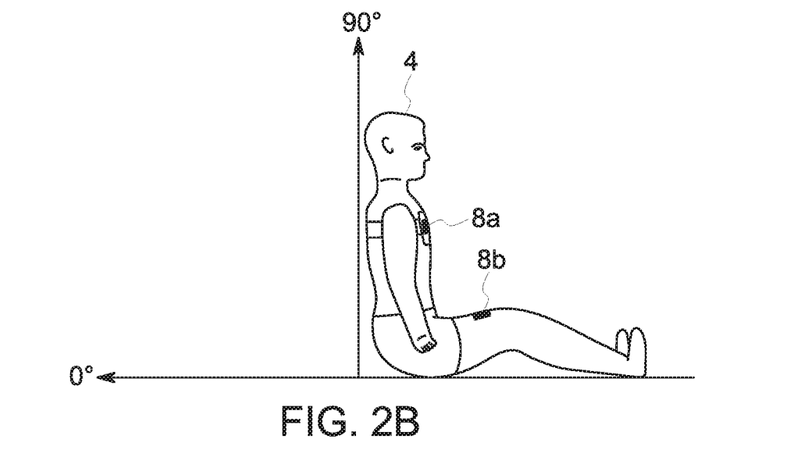

The activity sensors 8a-8c may be incorporated into the various sensing devices 3a-3c attached at various locations on the patient's body, or one or more activity sensors 8 may be stand alone devices attached at locations on the patient 4. FIGS. 2A and 2B illustrate an exemplary embodiment where one accelerometer 8a is incorporated into a sensing device 3 strapped to the patient's chest, which may be, for example, an ECG sensing device 3a. A second activity sensor 8b is attached to the patient's thigh. For example, the depicted arrangement of activity sensors 8a and 8b on the patient's torso and legs can be used to differentiate between a supine, seated upright, and standing position. For example, when the patient 4 is in the supine and standing positions both the activity sensors 8a and 8b will read the approximate orientation as one another—i.e. either both reading that the patient is lying horizontal or is standing vertically. However, when the patient is in the seated position as exemplified in FIG. 2B, the activity sensor 8a attached to the patient's chest will provide a different orientation than the activity sensor 8b attached to the patient's leg. Additionally, the depicted activity sensor 8a, 8b arrangement can also be arranged to sense information about the patient's motion, such as whether the patient is walking, where significant orientation changes would be detected in the activity sensor 8b on the patient's leg with lesser acceleration and/or orientation changes measured by the activity sensor 8a on the patient's chest.

The activity information may be received by the activity analysis module 26 in the hub device 15, such as transmitted via the respective communication link 11a-11c between the sensing devices 3a-3c and the hub 15. The activity analysis module 26 determines at least one of a position indicator 63 and a motion indicator 65 (FIG. 3) based on the information received from the activity sensor 8a-8c. For example, the position indicator 63 may indicate one of a predetermined set of positions for the patient. For instance, the activity analysis module 26 may select the position indicator 63 from a predefined list of positions, including supine, reclined, seated upright, standing upright, kneeling, bent forward, or the like. Alternatively or additionally, the activity analysis module 26 may determine a motion indicator 65 based on information from the activity sensors 8a-8c. The motion indicator 65 may be, for example, one of a predefined list of motion, including slow walking, fast walking, running, jumping, stair climbing, stationary with arm motion, stationary with leg motion, or the like. The position indicator 63 and/or motion indicator 65 may then be used by the activity tracking module 24 to determine the activity indicator 70. For example, the patient activity indicator 70 may take into account the patient location 68 to provide context for interpreting the position indicator 63 and/or motion indicator 65. For example, recorded arm motion or leg motion may be interpreted differently, and thus a different patient activity indicator 70 generated, depending on whether the patient location 68 is in the patient's bed versus in physical therapy.

Referring to the exemplary user interface display 56 shown in FIG. 4, the position and/or motion indicators for the patient may be reflected on the display, such as by the patient location indicator 54 for the respective patient 4. For example, the patient location indicator 54 may be provided in a particular shape, color, pattern, or by other visualization to indicate the patient's activity, such as the patient's position and/or motion. In the depicted embodiment, patients that are sitting or standing upright are illustrated by a solid patient location indicator and patients that are reclined or laying down are shown with a hollow patient location indicator 54.

Alternatively or additionally, the activity tracking module 24 may further account for physiological information recorded by one or more of the sensing devices 3a-3c. For example, the activity tracking module 24 may account for the patient's heart rate and/or breath rate when determining the patient activity indicator 70. For example, in an embodiment where the patient activity indicator 70 includes an activity level classification (e.g. level zero indicating very low activity and level five indicating high activity), the patient's heart rate and/or breath rate may be used to inform the activity level indication. Moreover, the activity tracking module 24a may further operate to instruct certain measurement modes for one or more of the sensing devices 3a-3c, such as instructing operation of the sensing devices to provide the physiological parameter data necessary to determine the patient activity indicator 70. For instance, the ECG sensing device 3a may be instructed to prioritize a heart rate determination and to cease or modify its recordation of ECG, such as reducing from a full twelve lead ECG recording to a three lead ECG recording.

The activity tracking module 24 may further be configured to determine a total activity indicator 71 based on the patient activity indicator 70 over a time period, and the activity threshold 67 may include requirements for the total activity indicator 71. For example, the time period may be set based on the patient's recovery needs as one or more time periods during which a particular activity should be performed by the patient. To provide just one explanatory example, prescribed activity requirements, or the patient's recovery plan, may require that the patient stand up at least once every four hours throughout a day, and/or that a patient go on a walk at least twice a day, or the like. The activity thresholds 67 are set accordingly. The total activity indicator then keeps track of the patient's activity indicator 70 over time by calculating a total activity indicator 71 for the appropriate time period(s) to determine whether the particular activity thresholds 67 are met, such as whether the patient stands up within the predetermined four hour time period or takes the required two walks over the course of the day.

Figure 5:
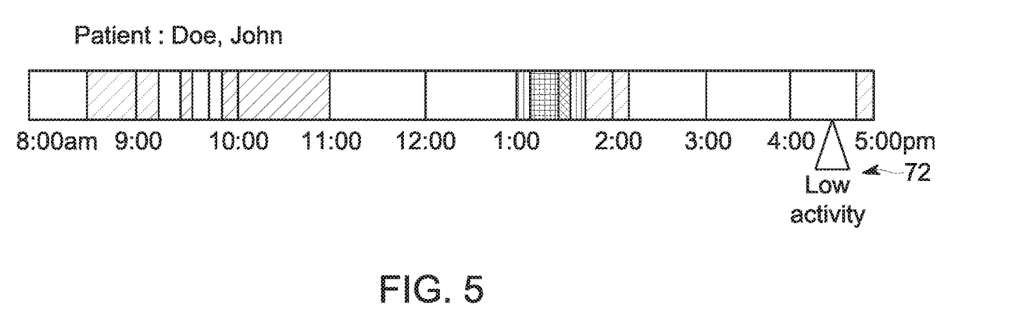
FIG. 5 is an exemplary visual display of a patient's activity level over time.

As described above, the activity alert 72 is generated by the activity tracking module 24 based on the comparison between the patient activity indicator 70, which may also be the total activity indicator 71 and the activity threshold 67. For example, the activity alert 72 may alert a clinician to an activity deficiency for the patient. FIG. 4 illustrates one exemplary embodiment of such an activity alert 72 alerting the clinician to a patient that has an activity deficiency. In the exemplary user interface display 56 depicted in FIG. 4, an activity alert 72 is generated for the patient associated with room 12. Namely, the activity alert 72 in FIG. 4 provides a visual indication to a clinician that the patient in room 12 has not met one or more activity thresholds, thus indicating to the clinician that they should encourage that patient to engage in certain activities in order to meet the activity threshold prescribed for the patient. FIG. 5 depicts another embodiment of a display showing an activity indicator 72 for a particular patient.

FIG. 5 depicts one embodiment of a visual display showing the patient activity indicator 70 over a time period, which in the depicted example is between 8 a.m. and 5 p.m. In the exemplary embodiment, the visual display is a bar representing 8 a.m. on the left side and 5 p.m. on the right side, wherein the patient activity indicator 70 over the represented times is indicated in the bar, such as by a color or pattern indicating each activity that occurred at the corresponding time. For example, where the patient activity indicator 70 is represented as an activity level between zero and five, each level may be associated with a color and/or a pattern that gets added to the portion of the display representing the time period for which the patient activity indicator 70 was calculated.

Referencing the example of FIG. 5, the total activity indicator 71 may be calculated for the entire represented time period, and/or a portion thereof. For example, multiple total activity indicators 71 may be calculated focusing on different time periods for assessment of different activity thresholds 67. For example, if an activity threshold 67 requires that a patient stand up at least once every four hours, then the total activity indicator 71 may keep a running three-hour count of whether the patient has stood up and/or the amount of time that the position indicator 63 has indicated an upright standing position. For example, the activity alert 72 depicted in the exemplary display in FIG. 5 may be generated based on the patient's prolonged period of inactivity as shown in the display, which may be reflected in the total activity indicator 71 value.

The hub device 15 may further include a display 16 and a speaker 18 that may be used to generate an alert or alarm, such as the activity alert or an alert regarding an alarm condition. Specifically, if an activity alert 72 is generated or one or more alarm limits are met, the computing system 135 of the hub 15 may control the display 16 to generate a visual alert, and/or may control the speaker 18 to generate an auditory alert. The display 16 may be any type of digitally-controlled visual display, and may further be a touchscreen controllable by a user to provide input to the hub 15, such as to silence an alert or alarm. The activity alert 72 may be generated by the display 16 and/or by the speaker 18. Alternatively or additionally, the activity alert 72 may be generated at a central monitoring station 50, such as may be provided at a nurses' station or other central location where clinicians can be accessed. The central monitoring station 50 includes a display 52 and speaker 53, each of which may selectively be used to generate an activity alert 72 according to instructions by the activity tracking module. For example, the alert may be generated at the central monitoring station closest to the patient's location, which may be in addition to or in alternative to generating the alert locally at the hub 15 or some other audio or visual alert generator at the patient's location.

The activity tracking module 24 is a set of software instructions executed on one or more processors within the patient monitoring system 1. In various embodiments, the activity tracking module 24 may be stored and executed within a computing system 235 of the host network 30. Alternatively or additionally, the activity tracking module 24 may be contained locally within the physiological monitoring system attached to or associated with the patient. For example, the activity tracking module 24 may be stored in and executed by a computing system 135 within the hub 15 and/or in one or more of the sensing devices 3a-3c. Further, in certain embodiments, the activity tracking module 24 may be provided in multiple devices within the system 1, such as to carry out various aspects or steps of the methods described herein. In the embodiment of FIG. 1, the activity tracking module 24 is comprised of instructions contained in and executed by both the computing system 235 of the host network 30 and the computing system 135 of the hub 15. Specifically, activity tracking module portion 24a is stored within the storage system of the computing system 235, and activity tracking module portion 24b is stored within the storage system 141 of the computing system 135. Together, the activity tracking module portions 24a, 24b execute instructions to determine the patient activity indicator 70 based on the patient location in the care facility and/or other considerations, as described herein. In other embodiments, the activity tracking module 24 may be entirely contained in either the computing system 235 of the host network 30 or the computing system 135 of the hub 15.

For example, in one embodiment the activity tracking module portion 24a in the host network may receive the patient location from the location tracking module 22 and determine the patient activity indicator 70, total activity indicator 71, and activity alert 72. The patient activity indicator 70, total activity indicator 71, and activity alert 72 may then be communicated to the hub 15 via the communication link 28 between receiver/transmitter 31 of the host network 30 and receiver/transmitter 29 of the hub 15. Such wireless communications may be conducted according to any of various wireless means, as is described above. In certain embodiments, the activity tracking module portion 24a may instruct the host network 30 to publish the patient activity indicator 70, total activity indicator 71, and/or activity alert 72, which may then be accessed by the hub 15 according to its own routine and timing. For example, communication of the activity indicators 70, 72 from the host network 30 to the hub 15 may be via a publish-subscribe messaging pattern, or model. In such an embodiment, the host network 30 publishes the activity indicator(s) 70, 72, and the hub 15 subscribes to the published "messages" containing the activity indicator(s) 70, 72. Accordingly, the host network 30 does not need to establish a direct communication link with the hub 15, and vice versa, and each can continue to operate normally regardless of the other.

Figure 3:
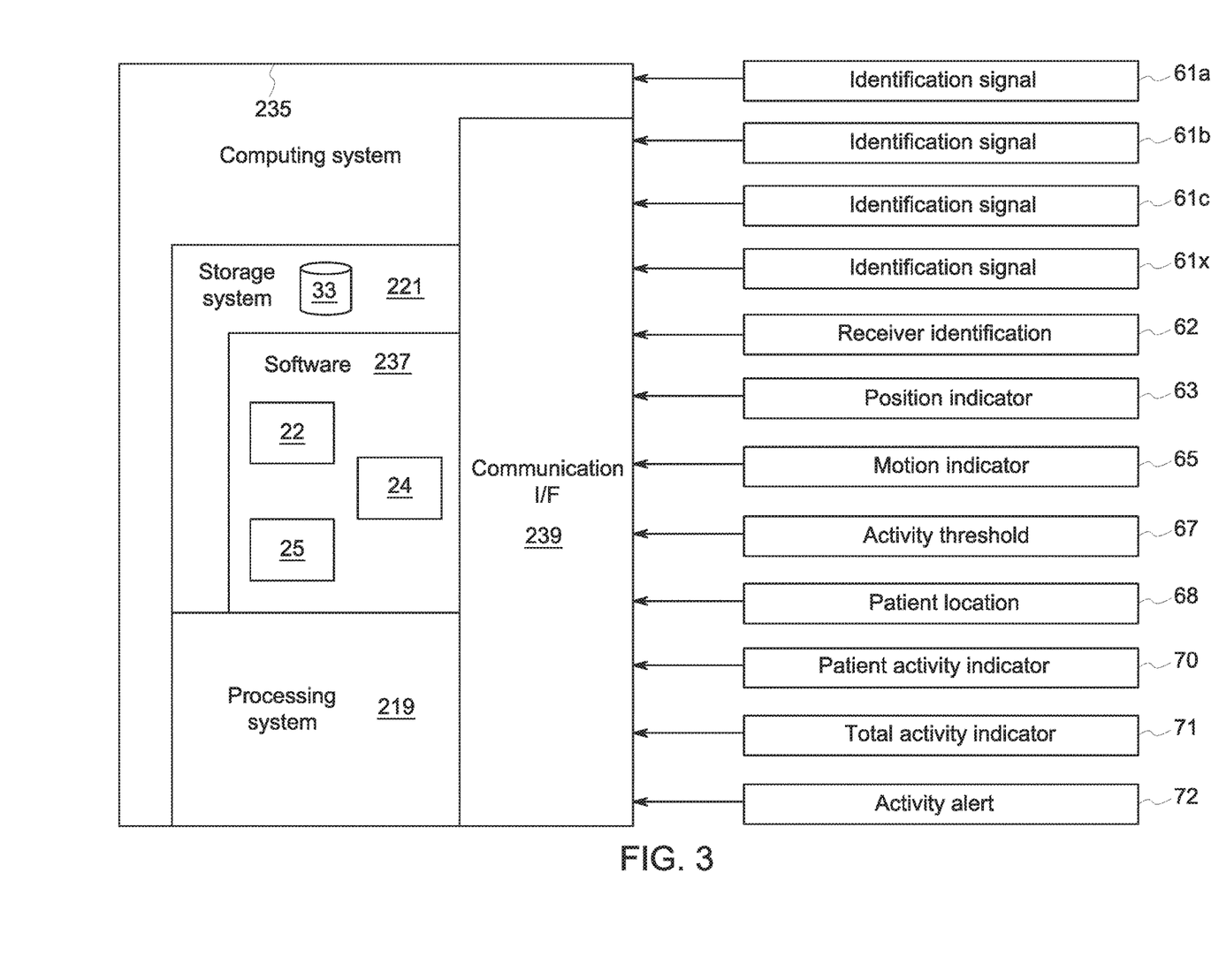
FIG. 3 is a schematic diagram of a computing system containing an activity tracking module as part of a patient monitoring system.

FIG. 3 schematically depicts one embodiment of computing system 235 of the host network 30. The exemplary computing system 235 includes the activity tracking module 24 the location tracking module 22 for determining the patient location 68, and the central monitoring module 25 that cooperates with the monitoring regulation module 23 to generate activity alerts 72 for the patient 4, which each function variously as described herein. The computing system 235 generally includes a processing system 219, storage system 221, software 237, communication interface 239. The processing system 219 loads and executes software 237 from the storage system 221, including the location tracking module 22, the activity tracking module 24, and the central monitoring module 25, which are applications within the software 237. Each of the modules 22, 24, 25 include computer-readable instructions that, when executed by the computing system 235 (including the processing system 219), direct the processing system 219 to operate as described in herein in further detail, including to execute the steps to determine a patient location 68 and the patient activity indicator 70.

Although the computing system 235 as depicted in FIG. 3 includes one software 237 encapsulating one location tracking module 22, the activity tracking module 24, and the central monitoring module 25, it should be understood that one or more software elements having one or more modules may provide the same operation. For example, the modules 22, 24, 25 may be combined into a shared set of instructions carrying out the steps described herein, or may be divided into any number of modules, which may be stored on separate storage devices and executed by different processing systems. Similarly, while description as provided herein refers to a computing system 235 and a processing system 219, it is to be recognized that implementations of such systems can be performed using one or more processors, which may be communicatively connected, and such implementations are considered to be within the scope of the description. For example, the computing system 235 may represent a cloud computing system and application implemented across multiple networked processing and storage devices.

The processing system 219 may include any one or more processing devices, such as one or more microprocessors, general purpose central processing units, application-specific processors, microcontrollers, or any other type of logic-based devices. The processing system 219 may also include circuitry that retrieves and executes software 237 from storage system 221. Processing system 219 can be implemented within a single processing device but can also be distributed across multiple processing devices or subsystems that cooperate in executing program instructions, such as in the cloud-computing application described above.

The storage system 221, which includes the patient medical record database 33, can comprise any storage media, or group of storage media, readable by processing system 219, and capable of storing software 237. The storage system 221 can include volatile and non-volatile, removable and non-removable media implemented in any method or technology for storage of information, such as computer-readable instructions, data structures, program modules, or other data. Storage system 221 can be implemented as a single storage device but may also be implemented across multiple storage devices or sub-systems. For example, the software 237 may be stored on a separate storage device than the medical record database 33. Likewise, medical record database 33 can be stored, distributed, and/or implemented across one or more storage media or group of storage medias. Similarly, medical record database 33 may encompass multiple different sub-databases at different storage locations and/or containing different information which may be stored in different formats. Storage system 221 can further include additional elements, such a controller capable of communicating with the processing system 219.

Examples of storage media include random access memory, read only memory, optical discs, flash memory, virtual memory, and non-virtual memory, magnetic sets, magnetic tape, magnetic disc storage or other magnetic storage devices, or any other medium which can be used to store the desired information and that may be accessed by an instruction execution system, as well as any combination or variation thereof, or any other type of storage medium. Likewise, the storage media may be housed locally with the processing system 219, or may be distributed in one or more servers, which may be at multiple locations and networked, such as in cloud computing applications and systems. In some implementations, the storage media can be a non-transitory storage media. In some implementations, at least a portion of the storage media may be transitory.

The communication interface 239 interfaces between the elements within the computing system 235 and external devices, such as various receiver/transmitters 31, 34a-34n that receive and transmit information to and from the host network 30. For example, the communication interface may operate to receive identification signals 61a-61c, 61x and the receiver identification 62 (providing the identification receiver 46a, 46n that received the identification signal(s)) generated via the location tracking system 40, receive position indicator(s) 63 and motion indicator(s) 65 from the hub 15 and/or directly from one or more of the sensing devices 3a-3c as well as the activity threshold(s) 67. The communication interface may further facilitate transmission of the patient location 68 and the activity indicators 70, 71, as well as the activity alert 72.

Figure 6:
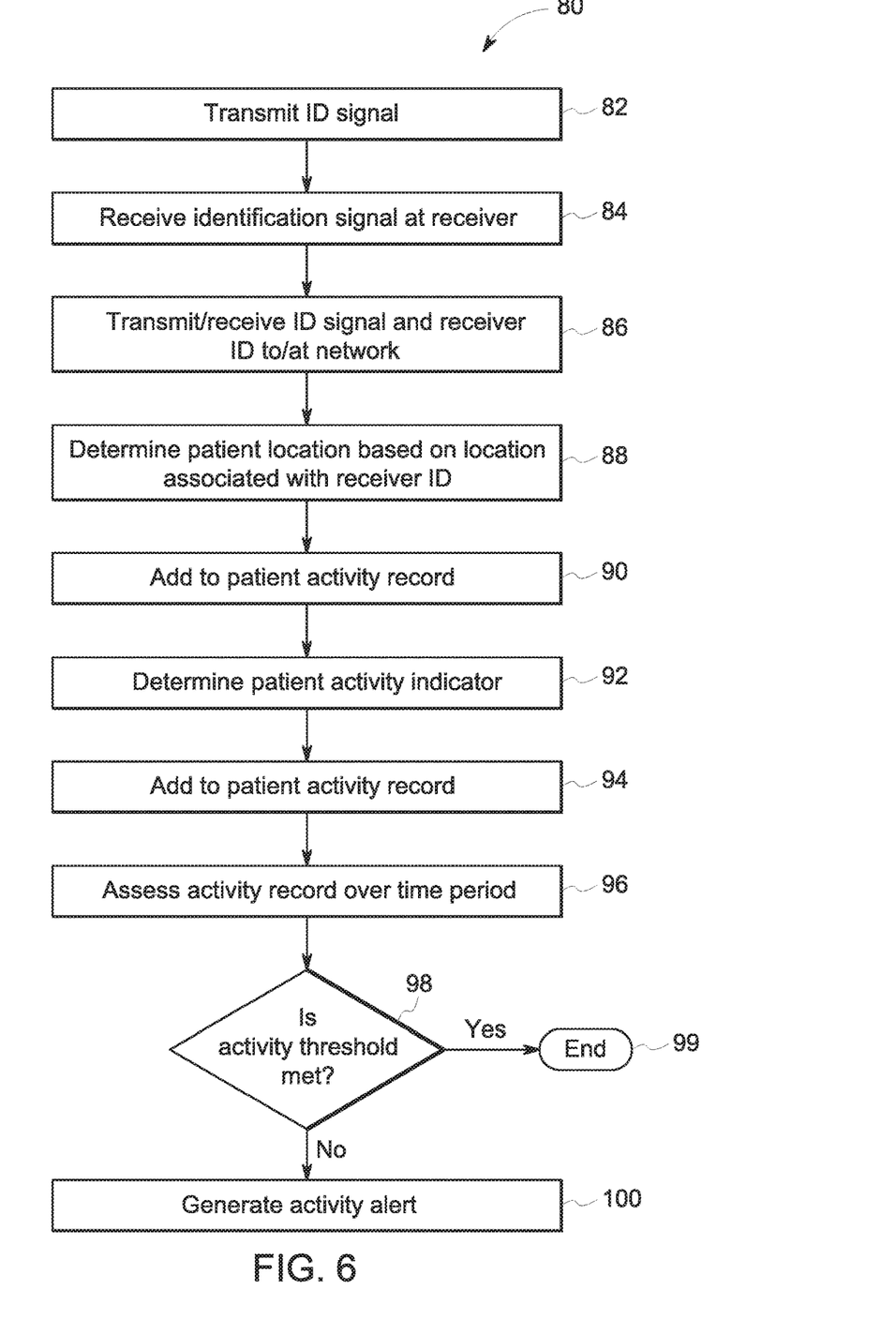
FIGS. 6-7 depict various embodiments of patient monitoring methods providing activity tracking.

FIGS. 6 and 7 depict various embodiments and aspects of a method 80 of monitoring a patient. In the embodiment depicted in FIG. 6, an identification signal is transmitted at step 82 and received by an identification receiver at step 84. The identification signal and receiver identification are then transmitted to and received at the host network, represented at step 86. The patient location is then determined at step 88 based on the location associated with the receiver identification and based on the patient associated with the identification signal. The patient location is then recorded in a patient activity record at step 90, such as in the patient medical record in the medical records database 33. A patient activity indicator is determined at step 92 based on the patient location, and the patient activity indicator is added to the patient activity record at step 94. The patient activity record may be a record generated by the activity tracking module 24 which records and reports a patient's activity and location throughout their stay in a care facility. Steps may then be executed to assess the patient's activity record over a time period, represented at step 96. For example, one or more total activity indicators 71 may be calculated or determined based on the patient activity record—e.g. the patient activity indicator 70 and the patient location 68 over the time period—which may then be compared to a respective activity threshold 67. If the activity threshold is met at step 98, then the method ends at step 99. However, if the activity threshold is not met, then an activity alert is generated at step 100, which may be, for example, generated on the display 16 of the hub 15 and/or on the display 52 of the central monitoring station 50.

Figure 7:
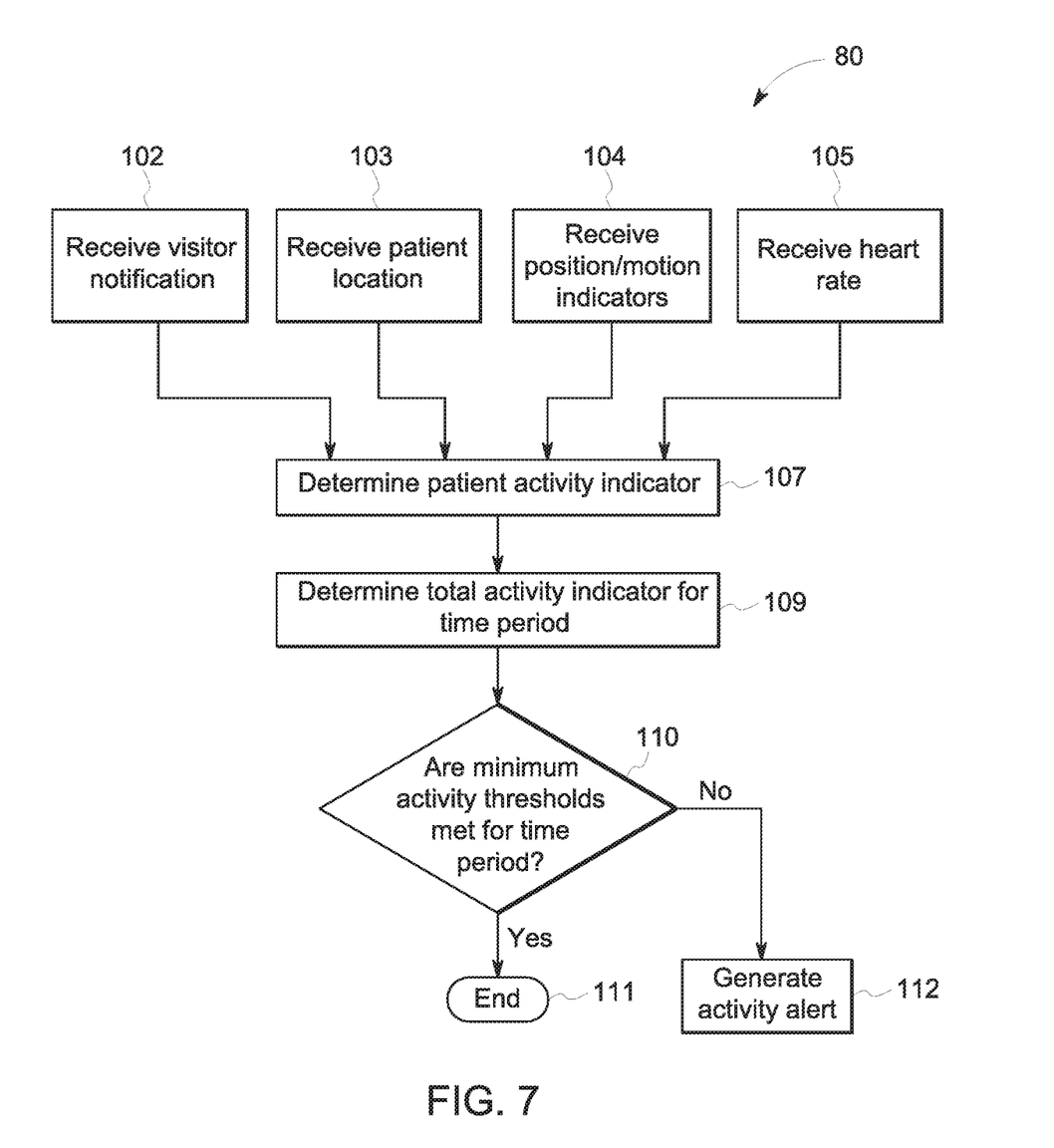

FIG. 7 depicts another embodiment of a method 80 for monitoring a patient. In the depicted embodiment, a visitor notification is received at step 102 indicating that a visitor identification transmitter 74 has been detected at the patient location 68. The patient location is received at step 103, such as from the location tracking module 22 in the location tracking system 40. Position and/or motion indicators are received at step 104, such as from the activity analysis module 26 associated with the activity sensors 8a-8c. A heart rate is received at step 105, such as measured by the ECG sensing device 3a. A patient activity indicator is then determined at step 107 based on the information received at steps 102-105. To provide just one example, the activity indicator may be determined based on a lookup table providing activity indicators based on a range of heart rates, position and/or motion indicators, and patient locations. The activity indicator may further account for the visitor notification, such as by a formula, or set of rules, dictating modification of the activity indicator value based on the presence or absence of a visitor. In other embodiments, the visitor notification may be separately tracked and may not be accounted for in the patient activity indicator 70 value. A total activity indicator is then determined over a time period at step 109. Instructions are executed at step 110 to determine whether minimum activity requirements, or thresholds, are met for the given timeframe. If all activity thresholds are met at step 110, then the method is terminated at step 111. If one or more of the activity threshold is not met, then an activity alert is generated at step 112, such as illustrated in the exemplary user interface display depicted at FIGS. 4 and 5.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

We claim:

1. A patient monitoring system comprising:
   an identification transmitter that transmits an identification signal, wherein the identification signal is associated with a patient;
   a location tracking system having a plurality of identification receivers arranged in a care facility that receive the identification signal from the identification transmitter, wherein the location tracking system determines a patient location within the care facility based on a location of receipt of the identification signal;
   at least two activity sensors attached to the patient measuring at least one of a position and a motion of the patient, each activity sensor comprising at least one of an accelerometer and a gyroscope; and
   an activity analysis module executable to determine at least one of a motion indicator or a position indicator based on measurements by the at least one of the at least two activity sensors;
   an activity tracking module executable to:
      receive at least one activity threshold for the patient wherein the activity threshold includes a prescribed activity requirement for a time period;
      receive the patient location;
      determine at least one patient activity indicator, wherein each patient activity indicator is based on the patient location and at least one of the motion indicator and the position indicator, wherein the patient activity indicator describes an activity or activity class;
      determine a total patient activity indicator based on a time series of the patient activity indicators;
      compare the total patient activity indicator to the activity threshold for the time period; and
      generate an activity alert based on the comparison between the total patient activity indicator and the activity threshold.

2. The patient monitoring system of claim 1, further comprising a sensing device configured to measure physiologic parameter data from the patient, wherein the physiologic parameter data includes a heart rate; and
   wherein the patient activity indicator is determined based further on the heart rate.

3. The patient monitoring system of claim 2, wherein the sensing device includes the identification transmitter and the at least one of the at least two activity sensors.

4. The patient monitoring system of claim 1, wherein the activity threshold includes a series of position indicators or motion indicators during the time period, and wherein the time series of the patient activity indicators of the total activity indicator is compared to the series of position or motion indicators.

5. The patient monitoring system of claim 1, wherein the activity tracking module is further executable to generate a visual display of the total patient activity indicator over the time period.

6. The patient monitoring system of claim 1, wherein the activity alert includes a visual indicator on at least one of a display of a hub device associated with the patient or on a display of a central monitoring station.

7. The patient monitoring system of claim 6, wherein the activity tracking module generates the activity alert when the total patient activity indicator is less than the activity threshold.

8. The patient monitoring system of claim 1, further comprising a visitor identification transmitter that transmits a visitor identification signal associated with a visitor, and wherein the location tracking system receives the visitor identification signal and determines a visitor location within the care facility based on a location of receipt of the visitor identification signal; and     wherein the activity tracking module is further executable to:

receive a visitor notification of the visitor location that is the same as the patient location;

determine the patient activity indicator based further on the visitor notification.

9. A method of monitoring a patient, the method comprising:

transmitting an identification signal associated with the patient from an identification transmitter;

receiving the identification signal at an identification receiver;

wherein one of the identification receiver or the identification transmitter is at a known location within a care facility;

determining a patient location within the care facility based on the known location of the identification receiver or the identification transmitter;

measuring at least one of a position and a motion of the patient;

determining at least one of a motion indicator or a position indicator;

determine at least one patient activity indicator, wherein each patient activity indicator is based on the patient location and at least one of the motion indicator and the position indicator, wherein the patient activity indicator describes an activity or activity class;

determining a total activity indicator based on a time series of the patient activity indicators;

comparing the total activity indicator to one or more activity thresholds for a time period; and     generating an activity alert based on a comparison between the total activity indicator and the one or more activity thresholds for the time period.

10. The method of claim 9, further comprising measuring at least one of the position and the motion of the patient with at least two activity sensors attached to the patient, each activity sensor comprising at least one of an accelerometer and a gyroscope.

11. The method of claim 9, further comprising measuring a heart rate, and wherein the patient activity indicator is determined based further on the heart rate.

12. The method of claim 9, further comprising storing the patient activity indicator over a time period for display, and generating a visual display of the patient activity indicator over the time period for display.

13. The method of claim 9, further comprising determining that the total activity indicator is less than the activity threshold, and wherein the activity alert includes a visual indicator on at least one of a display of a hub device associated with the patient or on a display of a central monitoring station indicating an activity deficiency for the patient.

14. The method of claim 9, further comprising receiving a visitor notification of a visitor location in the patient location;

determining the patient activity indicator based further on the visitor notification.

* * * * *